(12) United States Patent
Tzeng et al.

(10) Patent No.: US 6,706,060 B2
(45) Date of Patent: Mar. 16, 2004

(54) HEAT EXCHANGE CATHETER

(75) Inventors: Elbert Tzeng, Irvine, CA (US); Wesley Adzich, Yorba Linda, CA (US); Peter Barker, Oceanside, CA (US); Hortensia Pompa, San Clemente, CA (US); Scott M. Evans, Santa Ana, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/160,220

(22) Filed: May 30, 2002

(65) Prior Publication Data

US 2002/0183816 A1 Dec. 5, 2002

Related U.S. Application Data

(60) Provisional application No. 60/295,928, filed on Jun. 5, 2001.

(51) Int. Cl.[7] .................................................. A61F 7/00

(52) U.S. Cl. ...................... 607/105; 607/106; 607/113

(58) Field of Search ........................... 607/96, 104–107, 607/113; 604/113; 606/21–26

(56) References Cited

U.S. PATENT DOCUMENTS

| | | | |
|---|---|---|---|
| 6,231,594 B1 | * | 5/2001 | Dae ............................. 607/96 |
| 6,540,771 B2 | * | 4/2003 | Dobak et al. ............... 607/105 |
| 6,554,797 B1 | * | 4/2003 | Worthen ..................... 604/113 |

* cited by examiner

*Primary Examiner*—Roy D. Gibson
(74) *Attorney, Agent, or Firm*—John L. Rogitz

(57) ABSTRACT

A heat exchange catheter has a catheter body with a working fluid supply lumen extending therethrough, and terminating in a helical heat exchange tube that exits the body and extends proximally back along the catheter body. Working fluid flows through the heat exchange tube to exchange heat with the central venous system of a patient when the catheter body is properly placed in the patient.

2 Claims, 2 Drawing Sheets

HEAT EXCHANGE CATHETER

This application claims the benefit of Provisional Application No. 60/295,928 filed Jun. 5, 2001.

FIELD OF THE INVENTION

The present invention relates generally to heat exchange catheters.

BACKGROUND

The present assignee has provided heat exchange catheters for controlling a patient's temperature at normothermia to alleviate fever, which is standard of care for neuronally injured patients, and for establishing mild to moderate hypothermia in patients presenting symptoms of stroke, cardiac arrest, myocardial infarction, high intercranial pressure, brain trauma, and other neuronal injury-related diseases. The catheters can be used for controlled rewarming of the patients. Examples of such catheters are disclosed in U.S. Pat. Nos. 6,149,670 and 6,126,684, incorporated herein by reference.

The present invention is directed to a heat exchange catheter with a relatively high heat transfer rate.

SUMMARY OF THE INVENTION

A heat exchange catheter includes a catheter body and a working fluid supply lumen in the body. A helical heat exchange tube communicates with the supply lumen and extends along the outside surface of the body for exchanging heat with a body fluid when the body is disposed in a patient.

In a preferred embodiment, the heat exchange tube establishes plural coils that are bonded to the body at respective bond points. The coils otherwise are distanced from the body when fluid is circulated through the heat exchange tube. In one preferred implementation, coolant flows distally through the supply lumen and generally proximally through the heat exchange tube.

As set forth further below, the preferred supply lumen is established by a supply tube, and the supply tube preferably is made integrally with the heat exchange tube. Also, at least two working lumens can extend through the catheter body and terminate at respective infusion ports that are longitudinally spaced from each other along the catheter body.

A proximal hub can be engaged with the body and can establish a suture anchor. One or more central venous components preferably communicate with the hub. Additionally, a heater/chiller communicates with the supply lumen and heat exchange tube via the hub to heat or cool the working fluid.

In another aspect, a catheter includes a body supplying working fluid from a proximal heater/chiller toward a distal location on the body. A helical tube surrounds part of the body and communicates with the working fluid such that blood can flow between the tube and body to exchange heat with the working fluid.

In still another aspect, a system for exchanging heat with a patient includes a heater/chiller supplying a working fluid, and a helical heat exchanger disposable in the patient and communicating with the heater/chiller. As contemplated herein, the heat exchanger establishes plural coils and an axis, with the coils being configured to allow blood flow between the coils and the axis and between the coils and a vessel wall.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
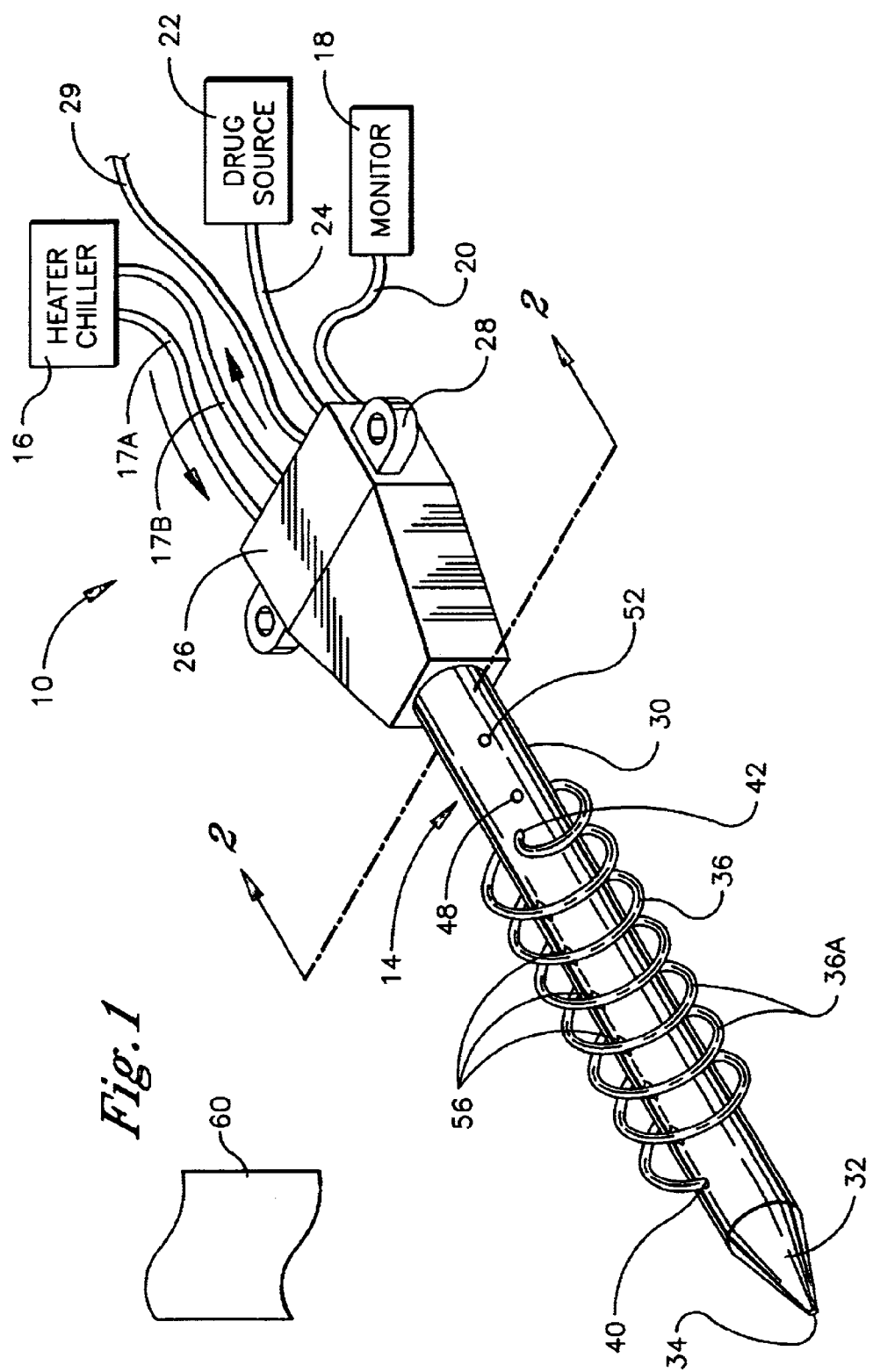
FIG. 1 is a perspective view of the present catheter, schematically showing the heater/chiller, drug source, and monitoring device.

Referring initially to FIG. 1, a system, generally designated 10, is shown for managing and otherwise controlling patient temperature while providing access to the central venous system of a patient. As shown, beginning at the proximal side of the system 10, the system 10 includes a central venous access and heat exchange catheter 14 that receives a heat exchange fluid (also referred to herein as "working fluid") from a heater/chiller 16, with the fluid circulating in a closed loop. The fluid preferably is saline, but other fluid such as refrigerant can be used. Either the fluid flow rate and/or the temperature of the fluid is controlled by a controller associated with the heater/chiller 16 based on a patient temperature feedback signal to control the amount and if desired the rate at which heat is added or subtracted from the patient. The controller can be implemented by a software-executing processor or by discrete logic circuits or other electronic circuitry device to establish a desired patient temperature by appropriately controlling the flow rate and/or heat exchanger in response to a temperature signal derived from a sensor in the patient. In any case, working fluid is supplied from the heater/chiller 16 via a working fluid supply line 17A, and working fluid returns to the heater/chiller 16 via a working fluid return line 17B.

As also shown in FIG. 1, at least two central venous (CV) components can be in communication with the catheter 14 for undertaking central venous functions in addition to controlling the temperature of the patient. These functions include and are not limited to drug infusion and blood extraction for blood monitoring, as well as blood pressure monitoring. For instance, a blood monitor 18 can communicate with the catheter 14 via a line 20 to monitor blood pressure or withdraw blood from the central venous system of the patient. Also, a drug source such as a syringe 22 can engage the catheter 14 via a connector with line 24 for infusing drugs or other medicament such as epinephrine into the patient. The components 16, 18, 22 can all be connected to the catheter 14 via a proximal connector hub 26 of the catheter 14. The hub 26 can be formed with a suture anchor 28 or other anchor structure such as tape for providing a means to fasten the catheter 14 to the skin of the patient for long-term use. Also, a guide wire lumen tube 29 is engaged with the hub 26 and extends therethrough to a guide wire lumen, described further below.

Turning to the portion of the system 10 distal to the hub 26, a preferably plastic, flexible catheter body 30 extends distally away from the hub 26. The body 30 is biocompatible, and can be coated with an anti-microbial agent and with an anti-clotting agent such as heparin. The body 30 can be a unitary piece of hollow plastic or it can be made of more than one coaxial tubes. Distally bonded to a portion of the body 30 is a comparatively more rigid frusto-conical shaped guide tip 32, an open distal end of which establishes a distal infusion port 34.

Figure 2:
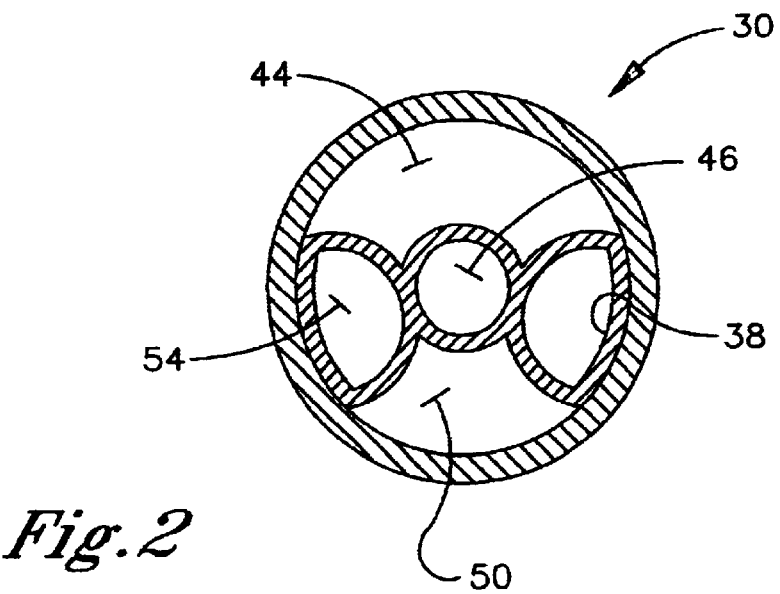
FIG. 2 is a transverse cross-sectional view, as seen along the line 2—2 in FIG. 1.
Figure 3:
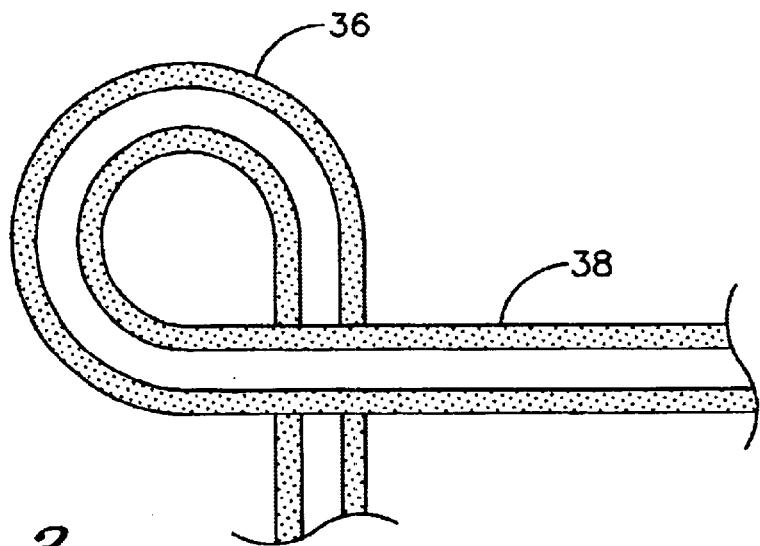
FIG. 3 is a longitudinal cross-section of the working fluid supply tube and helical return portion of the tube, with portions broken away.

A flexible, collapsible, helical-shaped heat exchange tube 36 surrounds the body 30. The heat exchange tube 36 can be made of plural discrete coils that are formed separately from each other and then joined together to communicate with each other, but more preferably the tube 36 is a single, unitarily-made tube made of very thin balloon material that extends from and indeed can be made unitarily or integrally with a working fluid supply tube 38 (FIGS. 2 and 3) that extends through the catheter body 30 and that communicates, via the hub 26, with the working fluid supply tube 17A from the heater/chiller 16. In any case, the heat exchange tube 36 exits the body 30 at a distal exit location 40, extends helically around the body, and reenters the body 30 at a proximal entry point 42, to join a working fluid return lumen 44 (FIG. 2) in the catheter 14. The working fluid return lumen 44 communicates with the working fluid return tube 17B via the hub 26. Thus, working fluid flows distally through the working fluid supply tube 38, into the helical heat exchange tube 36, and then proximally back through the heat exchange tube 36 to the proximal entry point 42.

In addition to the working fluid supply tube 38 and return lumen 44, the catheter 14 has at least two and possibly more, preferably three, infusion or working lumens for undertaking CV functions simultaneously with controlling patient temperature. Specifically, as shown in cross-reference to FIGS. 1 and 2, a first infusion or working lumen 54 terminates in a medial outlet port 48, and a second infusion or working lumen 50 terminates in a proximal outlet port 52. Both lumens 54, 50 are separated from the working fluid and both extend to the hub 26 shown in FIG. 1. In contrast, a guide wire tube 46, which communicates with the tube 29 shown in FIG. 1, extends to the distal port 34. In any case, to provide for mixing of infused drugs in the bloodstream if two drugs are to be administered, the ports 34, 48, 52 are longitudinally separated from each other as shown. With the above in mind, the monitor 18 (FIG. 1) or other CV device such as an infusion device can communicate with one of the infusion or working lumens 54, 50 while the syringe 22 can communicate with the other infusion or working lumen 50, 54.

While the Figures show that some of the lumens in the catheter 14 are established by respective tubes within the body 30 and some of the lumens are established in part by the catheter body 30 itself, all lumens can be established by separate tubes within the body 30 or none need be. Also, the shape of the lumens is exemplary; any suitable lumen shapes are contemplated herein.

In the presently preferred embodiment, the helical heat exchange tube 36 establishes plural coils 36A. At least two and preferably all coils 36A are bonded to the body 30 (or to, e.g., the guide wire tube 46 that can form part of the body 30) at respective epoxy bonding locations 56. This prevents the tube 36 from bunching up when collapsed and withdrawn from the patient. A substrate 60 with printed instructions for use can be included in a kit along with the catheter 14.

The catheter 14 is advanced (possibly through an introducer sheath) into the vena cava of the patient through a groin entry point or through a neck entry point to the central venous system of the patient. When advanced through the groin the catheter is advanced either through the femoral vein to the iliac vein and then to the inferior vena cava, and when advanced through the neck into the jugular vein or advanced through the chest into the subclavian vein to the superior vena cava.

Working fluid is then circulated through the working fluid supply tube 38 and helical heat exchange tube 36, which inflates the tube 36 and causes it to be distanced from the catheter body 30 except at the bond points 56. This allows good blood flow between the tube 36 and body 30 around all exposed surfaces of the tube 36, promoting high heat exchange between the blood and the working fluid. To withdraw the catheter 14 from a patient, the working fluid supply and return lumens are disconnected from the heater/chiller 16 and the catheter 14 pulled proximally. As the catheter body 30 moves through the patient entry point, the heat exchange tube 36 is collapsed around the catheter body 30.

While the particular HEAT EXCHANGE CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for" or, in the case of a method claim, the element is recited as a "step" instead of an "act".

What is claimed is:

1. A heat exchange catheter, comprising:

a catheter body;

at least one working fluid supply lumen in the body; and at least one helical heat exchange tube communicating with the supply lumen and extending along an outside surface of the body for exchanging heat with a body fluid when the body is disposed in a patient, wherein the heat exchange rube establishes plural coils, and at least two coils are bonded to the body at respective bond points, the coils otherwise being distanced from the body when fluid is circulated through the heat exchange tube.

2. A hear exchange catheter, comprising:

a catheter body;

at least one working fluid supply lumen in the body; and at least one helical heat exchange tube communicating with the supply lumen and extending along an outside surface of the body for exchanging heat with a body fluid when the body is disposed in a patient, further comprising at least two working lumens extending at least part way through the catheter body and terminating at respective infusion ports, the infusion ports being longitudinally spaced from each other along the catheter body.

* * * * *